United States Patent [19]

Guttmann et al.

[11] Patent Number: 4,816,243

[45] Date of Patent: * Mar. 28, 1989

[54] PREPARATION OF VANADIUM III OXIDIC COMPOUNDS, AND DEHYDROGENATION OF PARAFFINS

[75] Inventors: Andrew T. Guttmann, Maple Heights; James F. Brazdil, Mayfield Village; Robert K. Grasselli, Aurora, all of Ohio

[73] Assignee: The Standard Oil Company, Cleveland, Ohio

[*] Notice: The portion of the term of this patent subsequent to Apr. 12, 2005 has been disclaimed.

[21] Appl. No.: 113,957

[22] Filed: Oct. 29, 1987

Related U.S. Application Data

[63] Continuation-in-part of Ser. No. 941,881, Dec. 15, 1986, Pat. No. 4,737,355.

[51] Int. Cl.$^4$ ............................................. C01F 1/00
[52] U.S. Cl. .................................... 423/593; 252/188.1; 252/188.25; 423/407; 423/594; 423/595; 423/598; 423/599; 423/600; 502/524; 502/525
[58] Field of Search ................................ 423/592, 593

[56] References Cited

U.S. PATENT DOCUMENTS

| | | | |
|---|---|---|---|
| 2,702,739 | 1/1955 | Kelly, Jr. ............................. | 423/592 |
| 3,410,652 | 11/1968 | Hausen et al. ...................... | 423/592 |
| 4,035,476 | 7/1977 | Kmaier et al. ....................... | 423/592 |
| 4,619,822 | 10/1986 | Hammon et al. ................... | 423/592 |
| 4,737,355 | 4/1988 | Guttmann et al. .................. | 423/593 |

FOREIGN PATENT DOCUMENTS

| | | | |
|---|---|---|---|
| 1478120 | 4/1967 | France ................................ | 423/592 |
| 1141622 | 6/1986 | Japan .................................. | 423/592 |

*Primary Examiner*—Asok Pal
*Attorney, Agent, or Firm*—C. S. Lynch; D. J. Untener; L. W. Evans

[57] ABSTRACT

Disclosed is making a particular inorganic crystalline vanadium III oxidic compound from a pentavalent vanadium compound and at least one other or more metal cations, which process comprises (1) reducing a pentavalent vanadium oxidic compound to the $V^{III}$ state by heating at 100° C. or less an aqueous medium slurry or solution of said pentavalent compound containing a reducing agent selected from hydrazine and hydrocarbylhydrazine, (2) providing in said aqueous medium, either before, during or after said reducing step, said other metal cation(s) in solution in the ratio called for by said particular crystalline compound, (3) removing the liquid aqueous medium, and (4) calcining the resulting dry solid at a temperature in the range from 400° to 800° C. in an inert atmosphere.

Also disclosed is the vapor phase catalytic dehydrogenation of paraffins using certain spinels and perovskites as catalysts.

2 Claims, No Drawings

PREPARATION OF VANADIUM III OXIDIC COMPOUNDS, AND DEHYDROGENATION OF PARAFFINS

This application is a continuation-in-part of Ser. No. 941,881, filed Dec. 15, 1986, now U.S. Pat. No. 4,737,355.

This invention relates to an improved method of making inorganic crystalline vanadium III oxidic compounds. These compounds are generically called vanadites.

In a more specific aspect the invention concerns an improved method of making $V^{III}$ crystalline spinel compounds and crystalline perovskite compounds.

The usual method of preparation of vanadites and related compounds consists of preparing an intimate physical mixture of the appropriate oxides, including a low-valent vanadium oxide such as $V_2O_3$, having the cations in the atomic ratios corresponding to that of the desired final composition, and heating this mixture to a temperature sufficiently high to cause the reaction of one solid with the other and the formation of a new phase. The oxide mixture is usually prepared by grinding, followed by pressing, pelleting, and firing at temperatures from about 700° to about 1200° C. The sequence of grinding, pressing, and firing has to be repeated several times in order to obtain a nearly homogeneous phase. Since both the lower vanadium oxides (e.g., $V_2O_3$), and the resulting products are unstable to air oxidation at high temperatures, the firing step is usually done in a vacuum, in an inert gas, or in a reducing atmosphere ($H_2$ or CO) (see e.g., Rogers et al., *J. Phys. Chem. Solids,* 24, 347–60 [1963], or H. Oshima, *J. Amer. Ceramic Soc.*, 63, 504–507 [1980]). The starting vanadium oxides themselves, such as $V_2O_3$, are prepared by hydrogen reduction of $V_2O_5$ at 650°–1000° C. It is thus evident that the prior art procedures for the synthesis of vanadites and the like are complicated, time- and energy-consuming, and require very high temperatures.

It is an object of the invention to provide an improved method to prepare crystalline vanadium III oxidic compounds.

It is an object of the present invention to prepare vanadium spinel compounds by an improved process.

It is an object of the present invention to prepare vanadium perovskite compounds by an improved process.

It is a further object of the invention to prepare vanadium spinels from 5-valent vanadium compounds without resorting to high temperatures to reduce the vanadium to a +3 valence.

It is a further object to provide a process for dehydrogenation of paraffins using the vanadium III oxidic compounds, such as the vanadium spinels, as catalysts.

Other objects, as well as features, aspects and advantages, of the invention will become apparent from a study of the specification.

The foregoing and other objects are realized by the present invention according to which there is provided a process for making a particular inorganic crystalline vanadium III oxidic compound from a pentavalent vanadium compound and at least one other or more metal cations, which process comprises (1) reducing a pentavalent vanadium oxidic compound to the $V^{III}$ state by heating at 100° C. or less an aqueous medium slurry or solution of said pentavalent compound containing a reducing agent selected from hydrazine and a hydrocarbylhydrazine, (2) providing in said aqueous medium, either before, during or after said reducing step, said other metal cation(s) in solution in the ratio called for by said particular crystalline compound, (3) removing the liquid aqueous medium, and (4) calcining the resulting dry solid at a temperature in the range from 400° to 800° C. in an inert atmosphere. Usually calcining temperatures are no more than 700° C.

Hydrazine is the now preferred reducing agent, but monohydrocarbylhydrazines (such as monoalkyl or monoarylhydrazines) are also especially suitable reducing agents. The hydrocarbyl group usually has 1–10 C atoms.

In a more specific aspect of the present invention there is provided a process for making a compound selected from a crystalline spinel of the formula

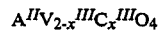    formula (1)

or a crystalline perovskite of the formula

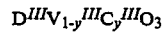    formula (2)

from a pentavalent vanadium compound, where A is one or more of Mg, Zn, Mn, Fe, Co, Ni, Cu and Cd; D is one or more of Y, the rare earths and Bi; C is one or more of Al, Ga, Cr, Fe and Co, x is zero to <2, usually zero to 1.9, and y is zero to <1, usually zero to 0.9, which process comprises (1) reducing a pentavalent vanadium oxidic compound to substantially the $V^{III}$ state by heating at 100° C. or less an aqueous medium slurry or solution of said pentavalent compound containing a reducing agent selected from hydrazine and a hydrocarbylhydrazine, (2) providing in said aqueous medium either before, during or after said reducing step, $A^{II}$, $D^{III}$ and $C^{III}$ cations in solution in the ratio called for by the selected formula, (3) removing the liquid aqueous medium, and (4) calcining the resulting dry solid at a temperature in the range from 400° to 800° C. in an inert atmosphere. Usually calcining temperatures are no more than 700° C.

In the foregoing, the rare earths are as recognized in the art: namely, atomic numbers 57 to 71.

The cations other than vanadium are usually added according to step (2) of the present process as salts of acids forming easily thermally destructible, non-oxidizing anions. Organic salts, such as acetates are often preferred.

In a now preferred aspect of the invention for making spinels of formula (1) where y is zero, hydrazine (in an amount of 0.5–3 moles per atom of $V^V$), is mixed with an aqueous solution of the $A^{II}$ salt of a carboxylic acid, particularly the $A^{II}$ acetate. To facilitate solubility, an additional amount of an organic carboxylic acid, such as acetic acid can be added. To the dispersion thus obtained, a compound of pentavalent vanadium, particularly ammonium metavanadate, is added slowly, at from about 30° to about 100° C., with agitation, as either a solid or an aqueous solution. After addition, the mixture is further stirred and heated, then evaporated and dried, preferably in an inert atmosphere, e.g., $N_2$. The dried material is then heated under an inert gas (nitrogen, argon, etc.) at from about 400° to about 700° C., for a period from 5 to 25 hours.

In the synthesis of vanadium-containing spinels according to the method of this invention, the X-ray powder diffraction analysis reveals, quite unexpectedly, the formation of a spinel structure at these low calcination temperatures. Moreover, the repetitive grinding and heating of the prior art methods are totally unnecessary.

The present invention described here is clearly superior to the prior art methods, since it allows preparation of vanadium III compounds spinels via aqueous low temperature reduction of the vanadium ion, followed by a calcination heat treatment at unexpectedly low temperatures. The formation of the desired crystalline phases at such low temperatures is particularly unexpected and unique.

According to another aspect of the invention, the spinels and perovskites defined in formula (1) and formula (2), where (2−x) and (1−y) are each at least 0.1, have been found to catalyze the dehydrogenation of $C_2-C_4$ paraffins to olefins, especially propane to propylene, at very high selectivities approaching 100 percent. The reaction can be effected at 450° to 700° C. at contact times of 0.2 to 40 seconds.

The crystalline vanadium III products made by the process of this invention are useful as ceramic coloring agents in enamels, glazes, and paints and as fillers and coloring agents in plastics such as polyethylene and polystyrene. In the plastics, they can be employed in amounts of 0.5% to 10% or even more, being milled with the plastics in finely divided form.

$V^{III}$ products can be used, for instance, in the following paint formula:

| Ingredient: | Lbs. |
|---|---|
| Crystalline III Product | 300 |
| Zinc Oxide | 25 |
| Long-Oil Soya Alkyd Resin (60% nonvolatile) | 480 |
| Mineral Spirits | 181 |
| Cobalt Naphthenate (6% Co) | 3 |
| Lead Naphthenate (24% Pb) | 3 |
| Calcium Naphthenate (4% Ca) | 2 |
| Total | 994 |

The following examples of the invention are illustrative and are not to be considered limiting. In the dehydrogenation examples, summarized in Table 1, the runs were effected in a fixed tubular bed of catalyst. In the spinel preparation examples, deoxygenated water was used to prepare the solutions and slurries, and the operations were carried out under nitrogen.

EXAMPLE 1

Crystalline $MgV_2O_4$ spinel was made as follows:

To a solution of 22.55 g $Mg(OAc)_2.4H_2O$ in 150 ml water, there was added 10.85 g hydrazine hydrate (97%). After warming to 65° C. 24.6 g $NH_4VO_3$ was added dry, in small portions, with vigorous agitation. The mixture became progressively darker. After stirring ½ hour at 65°-70° C., the mixture was evaporated under $N_2$ at 90° C. max. The thick viscous mass was dried over night in $N_2$ at 130°-140° C. The brown-black solid was then treated 2 h @350° C. and 3 h @420° C. under $N_2$; followed by 21 hours @700° C. in flowing argon (tube furnace). X-ray powder diffraction data showed that the product was a spinel.

Analysis: 53.0% V; 13.0% Mg; 34.0% 0 (by difference).

Calculated formula: $Mg_{1.03}V_2O_{4.09}$.

EXAMPLE 2

Crystalline $ZnV_2O_4$ spinel was made as follows:

To a solution of 23.08 g of Zinc acetate dihydrate in 150 ml of water was added 10.52 g of hydrazine monohydrate dropwise. A voluminous precipitate of $Zn(OH)_2$ was obtained. Another 150 ml of water was added with stirring. To the stirred slurry was slowly added 24.61 g of $NH_4VO_3$ (solid) at 65°-70° C. The mixture darkened slowly and became medium brown. On further evaporation at 85°-90° C., the residue thickened and became black-brown. It was dried overnight at 115°-130° C. It was then heated under nitrogen for 0.5 h at 500° C., 0.5 h at 600° C. and 24 h at 700° C. X-ray powder diffraction analysis showed the spinel structure.

Analysis: 42.8% V: 27.4% Zn: 29.8% 0 (by difference).

Calculated formula: $ZnV_2O_{4.4}$.

In Examples 3-5, summarized in Table 1, the vapor phase catalytic dehydrogenation of propane was effected at 500° C. in the presence of an equal volume of $N_2$ diluent, using the contact times shown. In Examples 3 and 4 the catalyst was the magnesium-vanadium spinel of Example 1, and 9 parts by weight were diluted with 1 part by weight silica. In Example 5 the catalyst was the zinc-vanadium spinel of Example 2, undiluted.

TABLE 1

| Example No. | Catalyst | Contact Time, Seconds | Propane Conversion, Percent | Selectivity to Propene, Percent |
|---|---|---|---|---|
| 3 | Mg/V spinel | 12.5 | 7.4 | 94.9 |
| 4 | Mg/V spinel | 26 | 7.3 | 97.0 |
| 5 | Zn/V spinel | 10.6 | 4.8 | 100 |

EXAMPLE 6

Crystalline $LaVO_3$ perovskite is made as follows:

To a solution of 72.04 g of $La(C_2H_3O_2)_3.1.5H_2O$ in 500 ml of water is added 10.52 g of hydrazine monohydrate. After warming to 65° C., 24.6 g $NH_4VO_3$ is added dry, in small portions, with vigorous agitation. After evaporation to near dryness, the solid mass is dried for 16 hours in $N_2$ at 130° C. The dried material is then heat treated under nitrogen for 2 hours at 350° C., 2 hours at 500° C. and 24 hours at 700° C.

EXAMPLE 7

Crystalline $LaCr_{0.5}V_{0.5}O_3$ perovskite is made as follows:

To a solution of 72.04 g of $La(C_2H_3O_2)_3.1.5H_2O$ in 500 ml of water is added 5.26 g of hydrazine monohydrate. After warming to 65° C., 12.31 g $NH_4VO_3$ is added dry, in small portions, with vigorous agitation followed by 25.95 g $Cr(C_2H_3O_2)_3.H_2O$. After evaporation to near dryness, the solid mass is dried for 16 hours in $N_2$ at 130° C. The dried material is then heat treated under nitrogen for 2 hours at 350° C., 2 hours at 500° C. and 24 hours at 700° C.

EXAMPLE 8

Crystalline $ZnFeVO_4$ spinel is made as follows:

To a solution of 23.08 g $Zn(C_2H_3O_2)_2.2H_2O$ in 300 ml of water is added 5.26 g of hydrazine monohydrate. After warming to 65° C., 12.31 g $NH_4VO_3$ is added dry, in small portions, with vigorous agitation followed by 33.92 g $Fe(C_3H_5O_3)_3$, ferric lactate. After evaporation to near dryness, the solid mass is dried for 16 hours in $N_2$ at 130° C. The dried material is then heat treated under nitrogen for 2 hours at 350° C., 2 hours at 500° C. and 24 hours at 700° C.

EXAMPLE 9

Crystalline $VNbO_4$ with the rutile structure is made as follows:

To 66.95 g of $Nb(C_2H_5O)_5$ is added 10.52 g of hydrazine monohydrate dropwise. 150 ml of water is added with stirring. After warming to about 65° C., 24.6 g $NH_4VO_3$ is added dry, in small portions, with vigorous stirring. After evaporation to near dryness, the solid mass is dried for 16 hours in $N_2$ at 120° C. The dried material is then heat treated under $N_2$ for 2 hours at 350° C., 2 hours at 500° C., and 24 hours at 700° C.

EXAMPLE 10

Crystalline $V_{0.1}Cr_{1.9}O_3$ solid solution with the corundum structure is made as follows:

To a solution of 95.17 g $Cr_2(C_2O_4)_2.6H_2O$ in 300 ml of water is added 1.05 g of hydrazine monohydrate dropwise. After warming to about 65° C., 2.46 g $NH_4VO_3$ is added dry, in small portions, with vigorous stirring. After evaporation to near dryness, the solid mass is dried for 16 hours in $N_2$ at 120° C. The dried material is then heat treated under $N_2$ for 2 hours at 350° C., 2 hours at 500° C., and 24 hours at 700° C.

EXAMPLE 11

Crystalline $VTaO_4$ with the rutile structure is made as follows:

To a mixture of 70.72 g $Ta(OCH_3)_5$ in 300 ml of water is added 10.52 g of hydrazine monohydrate dropwise. After warming to about 65° C., 24.6 g $NH_4VO_3$ is added dry, in small portions, with vigorous stirring. After evaporation to near dryness, the solid mass is dried for 16 hours in $N_2$ at 120° C. The dried material is then heat treated under $N_2$ for 2 hours at 350° C., 2 hours at 500° C., and 24 hours at 700° C.

As will be evident to those skilled in the art, various modifications of this invention can be made or followed in the light of the foregoing disclosure and discussion without departing from the spirit and scope of the disclosure or from the scope of the claims.

We claim:

1. A process for making a particular inorganic crystalline vanadium III oxidic compound from a pentavalent vanadium compound and at least one other or more metal cations, which process comprises (1) reducing a pentavalent vanadium oxidic compound to the $V^{III}$ state by heating at 100° C. or less an aqueous medium slurry or solution of said pentavalent compound containing a reducing agent selected from hydrazine and hydrocarbylhydrazine, (2) providing in said aqueous medium, either before, during or after said reducing step, said other metal cation(s) in solution in the ratio called for by said particular crystalline compound, (3) removing the liquid aqueous medium, and (4) calcining the resulting dry solid at a temperature in the range from 400° to 800° C. in an inert atmosphere.

2. A process of claim 1 wherein step (1) contains hydrazine as a reducing agent.

* * * * *